(12) United States Patent
Volk et al.

(10) Patent No.: US 10,835,340 B2
(45) Date of Patent: *Nov. 17, 2020

(54) PACKAGE FOR MEDICAL DEVICE WITH TRAY AND BUMPER

(71) Applicant: K2M, Inc., Leesburg, VA (US)

(72) Inventors: Stephanie Volk, Ashburn, VA (US); Patrick Froman, Lakeville, MN (US)

(73) Assignee: K2M, Inc., Leesburg, VA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/378,839

(22) Filed: Apr. 9, 2019

(65) Prior Publication Data

US 2019/0231469 A1 Aug. 1, 2019

Related U.S. Application Data

(63) Continuation of application No. 15/460,097, filed on Mar. 15, 2017, now Pat. No. 10,299,877.

(51) Int. Cl.
*A61B 50/33* (2016.01)
*B65D 77/04* (2006.01)
(Continued)

(52) U.S. Cl.
CPC .............. *A61B 50/33* (2016.02); *A47L 13/42* (2013.01); *A61B 50/20* (2016.02); *A61B 50/30* (2016.02);
(Continued)

(58) Field of Classification Search
CPC ......... A47L 13/42; A61B 17/00; A61B 50/00; A61B 50/20; A61B 50/30; A61B 50/33; A61B 2017/00424; A61B 2017/0046; A61B 2017/00473; A61B 2050/0005; A61B 2050/3006; B29C 65/00; B29C 65/48; B29C 65/4815; B29C 66/301; B29C 66/303; B29C 66/30321; B29C 66/748; B65D 25/06; B65D 43/02; B65D 77/04; B65D 77/046; B65D 77/26; B65D 81/02; B65D 81/05; B65D 85/30
(Continued)

(56) References Cited

U.S. PATENT DOCUMENTS 2,846,806 A 8/1958 Gaines
3,376,973 A 4/1968 Granowitz et al.
(Continued)

FOREIGN PATENT DOCUMENTS

WO 03079918 A1 10/2003
WO 2005016183 A1 2/2005

OTHER PUBLICATIONS

The Partial European Search Report for EP Application No. 16203879.8 dated Apr. 20, 2017.

*Primary Examiner* — Bryon P Gehman
(74) *Attorney, Agent, or Firm* — Lerner, David, Littenberg, Krumholz & Mentlik, LLP (57) ABSTRACT

A package including at least one bumper having an elliptical shape that extends from a first end to a second end along a first plane and having a protrusion that extends from a first front along a second plane; and a first tray having a first cavity that extends from a second front along the second plane, wherein the first cavity includes at least one groove configured and dimensioned to receive the at least one bumper.

20 Claims, 12 Drawing Sheets

(51) Int. Cl.
  *B65D 81/05* (2006.01)
  *B65D 43/02* (2006.01)
  *B65D 77/26* (2006.01)
  *A61B 50/20* (2016.01)
  *A61B 50/30* (2016.01)
  *B29C 65/48* (2006.01)
  *B29C 65/00* (2006.01)
  *A47L 13/42* (2006.01)
  *A61B 17/00* (2006.01)
  *A61B 50/00* (2016.01)

(52) U.S. Cl.
  CPC ........ *B29C 65/4815* (2013.01); *B29C 66/301* (2013.01); *B29C 66/30321* (2013.01); *B29C 66/748* (2013.01); *B65D 43/02* (2013.01); *B65D 77/046* (2013.01); *B65D 77/26* (2013.01); *B65D 81/05* (2013.01); *A61B 2017/0046* (2013.01); *A61B 2017/00424* (2013.01); *A61B 2017/00473* (2013.01); *A61B 2050/0065* (2016.02); *A61B 2050/3006* (2016.02)

(58) Field of Classification Search
  USPC .................................. 206/557–565, 591–592
  See application file for complete search history.

(56) References Cited

U.S. PATENT DOCUMENTS

| | | | |
|---|---|---|---|
| 3,444,994 A | 5/1969 | Kaepernick | |
| 3,554,429 A | 1/1971 | Cohen | |
| 3,613,879 A | 10/1971 | Kemble | |
| 3,616,898 A | 11/1971 | Massie | |
| 3,759,376 A | 9/1973 | Lisowski | |
| 3,972,418 A | 8/1976 | Schuler et al. | |
| 4,111,302 A | 9/1978 | Roth | |
| 4,142,632 A | 3/1979 | Sandel | |
| 4,324,331 A | 4/1982 | Ignasiak | |
| 4,482,053 A | 11/1984 | Alpern et al. | |
| 4,511,035 A | 4/1985 | Alpern | |
| 4,602,715 A * | 7/1986 | Sarver .................... | B65D 81/05 206/591 |
| 4,708,241 A | 11/1987 | Black | |
| 4,782,942 A | 11/1988 | Ashley et al. | |
| 4,842,141 A | 6/1989 | Segal | |
| 4,850,477 A | 7/1989 | Gelardi et al. | |
| 4,903,827 A | 2/1990 | Phelps et al. | |
| 4,945,710 A | 8/1990 | Hustad | |
| 4,978,510 A | 12/1990 | Smith | |
| 4,986,414 A | 1/1991 | Ashley et al. | |
| D315,868 S | 4/1991 | Gelardi et al. | |
| 5,076,431 A | 12/1991 | Thompson | |
| D326,409 S | 5/1992 | Krueger et al. | |
| 5,123,528 A | 6/1992 | Brown et al. | |
| 5,129,511 A | 7/1992 | Brown et al. | |
| 5,133,454 A | 7/1992 | Hammer | |
| 5,176,258 A | 1/1993 | Antal | |
| 5,246,109 A | 9/1993 | Markle et al. | |
| 5,277,299 A | 1/1994 | Holzwarth et al. | |
| 5,341,934 A | 8/1994 | Hsu | |
| 5,353,922 A | 10/1994 | Sinn | |
| 5,368,160 A | 11/1994 | Leuschen et al. | |
| 5,379,895 A | 1/1995 | Foslien | |
| 5,388,701 A | 2/1995 | Ridgeway | |
| 5,392,903 A | 2/1995 | Sinn | |
| 5,392,917 A | 2/1995 | Alpern et al. | |
| 5,405,000 A | 4/1995 | Hagedon et al. | |
| 5,405,005 A | 4/1995 | White | |
| 5,441,150 A | 8/1995 | Ma | |
| 5,447,234 A * | 9/1995 | Faulstick ............... | B65D 25/06 206/449 |
| 5,497,601 A | 3/1996 | Gonzalez | |
| 5,562,208 A | 10/1996 | Hasler et al. | |
| 5,590,778 A | 1/1997 | Dutchik | |
| 5,669,501 A | 9/1997 | Hissong et al. | |
| 5,685,429 A * | 11/1997 | Myers .................... | B65D 25/06 206/449 |
| 5,690,222 A | 11/1997 | Peters | |
| 5,772,025 A | 6/1998 | Chen et al. | |
| 6,182,480 B1 | 2/2001 | Kim | |
| 6,622,864 B1 | 9/2003 | Debbs et al. | |
| 6,783,004 B1 | 8/2004 | Rinner | |
| 6,814,236 B2 | 11/2004 | Roshdy | |
| 6,827,212 B2 | 12/2004 | Reaux | |
| 6,830,149 B2 | 12/2004 | Merboth et al. | |
| 6,843,374 B1 | 1/2005 | Li et al. | |
| 6,889,839 B1 | 5/2005 | Rosten et al. | |
| 6,915,901 B2 | 7/2005 | Feinberg et al. | |
| 6,994,213 B2 | 2/2006 | Giard, Jr. et al. | |
| 7,066,329 B2 | 6/2006 | Riley | |
| 7,270,235 B2 | 9/2007 | Chen | |
| 7,475,776 B2 | 1/2009 | Detruit et al. | |
| 7,650,991 B2 | 1/2010 | Hester et al. | |
| 7,770,728 B2 | 8/2010 | Kærn | |
| 7,832,560 B2 | 11/2010 | Tilton | |
| 7,931,143 B1 | 4/2011 | Lin | |
| 8,006,839 B2 | 8/2011 | Hafner | |
| 8,079,468 B2 | 12/2011 | Pleil et al. | |
| 8,096,420 B2 | 1/2012 | Marhsall et al. | |
| 8,112,973 B2 | 2/2012 | Fischer et al. | |
| 8,113,348 B2 | 2/2012 | Foster | |
| 8,177,066 B2 | 5/2012 | Tilton | |
| 8,240,468 B2 | 8/2012 | Wilkinson et al. | |
| 8,403,941 B2 | 3/2013 | Peterson et al. | |
| 8,413,811 B1 | 4/2013 | Arendt | |
| 8,496,690 B2 | 7/2013 | Sixto et al. | |
| 8,511,473 B1 | 8/2013 | Bontrager et al. | |
| 8,518,341 B2 | 8/2013 | Friderich et al. | |
| 8,584,853 B2 | 11/2013 | Knight et al. | |
| 8,701,890 B2 | 4/2014 | Bertazzoni et al. | |
| 8,701,891 B2 | 4/2014 | Bontrager et al. | |
| D712,279 S | 9/2014 | Akana et al. | |
| 9,017,851 B2 | 4/2015 | Felder et al. | |
| 9,095,848 B2 | 8/2015 | Carrel et al. | |
| 9,101,349 B2 | 8/2015 | Knight et al. | |
| D752,430 S | 3/2016 | Stevenson et al. | |
| 9,687,300 B2 | 6/2017 | Hartfelder et al. | |
| 9,707,039 B2 | 7/2017 | Grabowski et al. | |
| 10,086,131 B2 | 10/2018 | Okihara | |
| 10,245,025 B2 | 4/2019 | Prikril et al. | |
| 2002/0112981 A1 | 8/2002 | Cooper et al. | |
| 2002/0125158 A1 | 9/2002 | High et al. | |
| 2003/0121810 A1 | 7/2003 | Roshdy | |
| 2005/0017059 A1 | 1/2005 | Salani et al. | |
| 2005/0033430 A1 | 2/2005 | Powers et al. | |
| 2005/0173278 A1 | 8/2005 | Caron | |
| 2005/0241974 A1 | 11/2005 | Chen | |
| 2006/0243616 A1 | 11/2006 | Caron | |
| 2007/0034538 A1 | 2/2007 | Landis | |
| 2008/0029419 A1 | 2/2008 | Appelbaum | |
| 2008/0190794 A1 | 8/2008 | Farrar et al. | |
| 2008/0283443 A1 | 11/2008 | Green | |
| 2009/0266728 A1 | 10/2009 | Turner | |
| 2011/0113437 A1 | 5/2011 | Day | |
| 2011/0186456 A1 | 8/2011 | Bertazzoni et al. | |
| 2011/0288596 A1 | 11/2011 | Brand et al. | |
| 2012/0256748 A1 | 10/2012 | Russell et al. | |
| 2013/0233736 A1 | 9/2013 | Hess et al. | |
| 2014/0215976 A1 | 8/2014 | Maasarani | |
| 2014/0360900 A1 | 12/2014 | Mizuoka et al. | |
| 2015/0021221 A1 | 1/2015 | Hendrickson et al. | |
| 2016/0101891 A1 | 4/2016 | Bailey et al. | |
| 2016/0262905 A1 | 9/2016 | Prado et al. | |
| 2016/0304260 A1 | 10/2016 | Ann | |
| 2017/0056122 A1 | 3/2017 | Ramsey | |
| 2018/0263721 A1 | 9/2018 | Volk et al. | |

* cited by examiner

PACKAGE FOR MEDICAL DEVICE WITH TRAY AND BUMPER

CROSS-REFERENCE TO RELATED APPLICATION

The present application is a continuation of U.S. application Ser. No. 15/460,097, filed on Mar. 15, 2017, the disclosure of which is hereby incorporated by reference herein in its entirety.

FIELD OF THE INVENTION

The invention relates generally to a package including at least one bumper and at least one tray. The package can be a single or double sterile package containing a medical device.

BACKGROUND OF THE INVENTION

One type of packaging for sterile medical devices uses a double sterile package having a sealed primary package that contains the device and a secondary sealed package. The primary package is contained inside the secondary package, with the contents of both packages being in a sterile condition. The package must be able to resist variations in environmental conditions. Additionally, the sterile package must be able to be easily and quickly opened, without recourse to implements, thereby permitting the ready removal of the sterile contents without disrupting the sterility thereof. Further, the sterile package must provide protection to the medical device during shipment and storage.

BRIEF SUMMARY OF THE INVENTION

In an aspect, there is disclosed a package comprising at least one bumper having an elliptical shape that extends from a first end to a second end along a first plane and having a protrusion that extends from a first front along a second plane; and a first tray having a first cavity that extends from a second front along the second plane, wherein the first cavity includes at least one groove configured and dimensioned to receive the at least one bumper.

Additional objects and advantages of the invention will be set forth in part in the description which follows, and in part will be obvious from the description, or may be learned by practice of the invention. The objects and advantages of the invention will be realized and attained by means of the elements and combinations particularly pointed out in the appended claims.

It is to be understood that both the foregoing general description and the following detailed description are exemplary and explanatory only and are not restrictive of the invention, as claimed.

BRIEF DESCRIPTION OF THE DRAWINGS

Various embodiments of the present disclosure are described herein below with reference to the drawings, wherein.

DETAILED DESCRIPTION

Various embodiments will now be described in detail with reference to the drawings, wherein like reference numerals identify similar or identical elements. Additionally, in the drawings and in the description that follows, terms such as front, rear, upper, lower, top, bottom, and the similar directional terms are used simply for convenience of description and are not intended to limit the disclosure attached hereto.

The present disclosure is directed to a package 10 for a medical device 70. As shown in FIGS. 4A-7B, the package 10 can include at least one bumper 20 and a first tray 40. The package 10 can further include at least one of a second tray 60, a first lid 66, and a second lid 68. When assembled, the package 10 can provide double-sterile barrier packaging for a medical device 70. The package 10 can provide protection to the medical device 70 during shipping and storage and can enable sterile delivery to the operating room. Additionally, the at least one bumper 20 can be used to alter the interior dimensions of a first cavity 44 of the first tray 40 to allow different sized medical devices to be shipped and stored inside the package 10. This feature allows a user to employ the same type of package to various sized medical devices 70 resulting in an efficient and cost-saving package 10.

The package 10 can include at least one bumper 20 having an elliptical shape that extends from a first end 22 to a second end 24 along a first plane 26 and having a protrusion 28 that extends from a first front 30 along a second plane 32; and a first tray 40 having a first cavity 44 that extends from a second front 42 along the second plane 32; wherein the first cavity 44 includes at least one groove 46 that is configured and dimensioned to receive the at least one bumper 20.

Figure 1A:
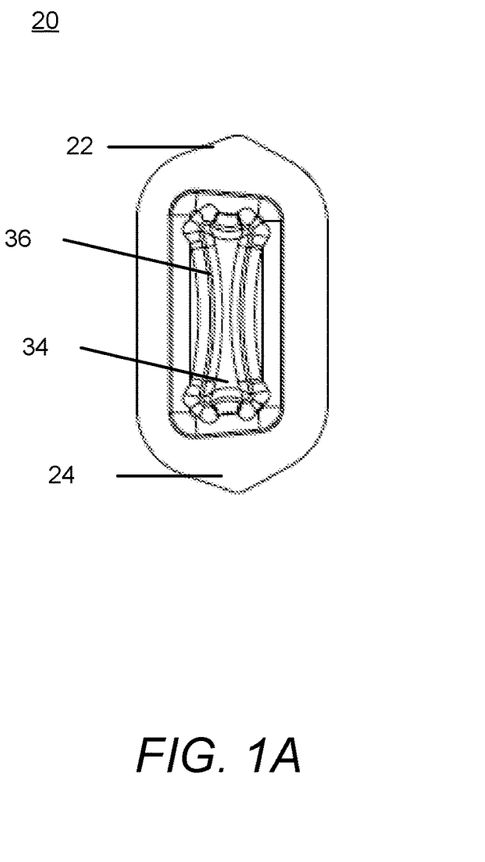
FIG. 1A is a top view of a bumper according to an aspect of the invention.
Figure 1B:
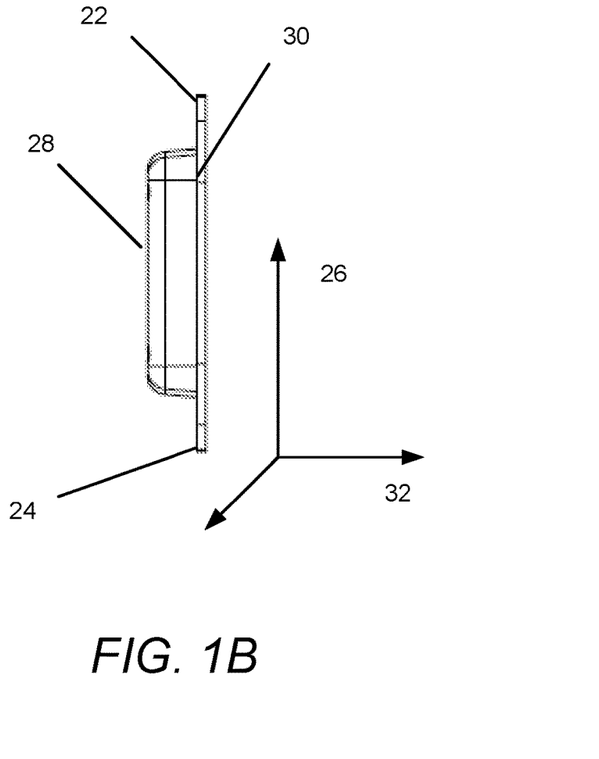
FIG. 1B is a side view of FIG. 1A.
Figure 1C:
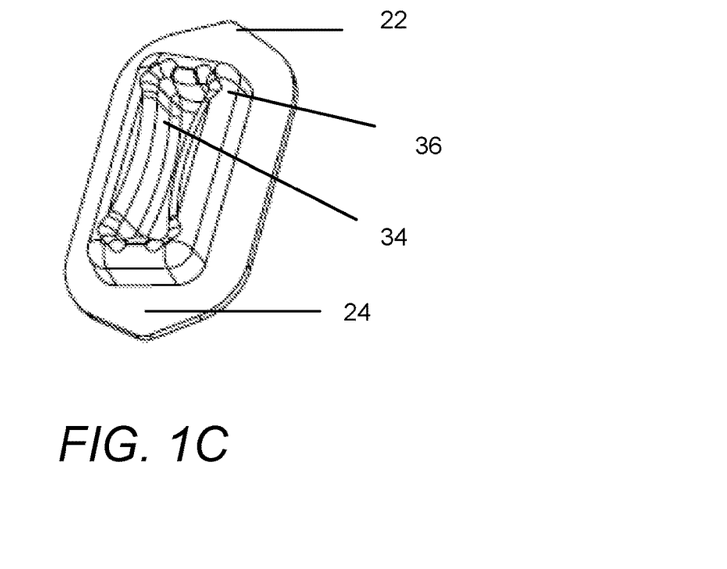
FIG. 1C is a perspective view of FIG. 1A.

As shown in FIGS. 1A-C, the at least one bumper 20 can have an elliptical shape that extends from a first end 22 to a second end 24 along a first plane 26 (e.g., a y-axis). Each of the first end 22 and the second end 24 can be independently configured and dimensioned to engage with at least one groove 46 of the first tray 40, as shown on FIG. 2A-B. In an aspect, each of the first end 22 and the second end 24 can be independently tapered. In another aspect, the first end 22 and the second end 24 can each be independently squared, rounded, or flat. In another aspect, the first end 22 and the second end 24 can each independently include a reverse taper, e.g., a notch (not shown) that extends toward a center of the bumper 20.

As shown in FIG. 1B, the at least one bumper 20 can have a protrusion 28 that extends from a first front 30 along a second plane 32 (e.g., an x-axis). In an aspect, the protrusion 28 can be configured and dimensioned to be any depth that can fit within a size defined by the at least one groove 46 and an end of the first cavity 44 of the first tray 40. In another aspect, the protrusion 28 can be configured and dimensioned to be any depth that can fit within a size defined by one groove 46 and another groove 46 of the first cavity 44 of the first tray 40.

As shown in FIGS. 1A and 1C, the protrusion 28 of the at least one bumper 20 can include sides 36 that define a hollow 34. The sides 36 of the protrusion 28 can increase the strength and decrease the crushability of the protrusion 28 during shipping and storage of the package 10. The hollow 34 can be in any shape, such as an hour glass, a rectangle, a square, a diamond, etc. In another aspect, the protrusion 28 can be fully extruded without a hollow (not shown).

Figure 4A:
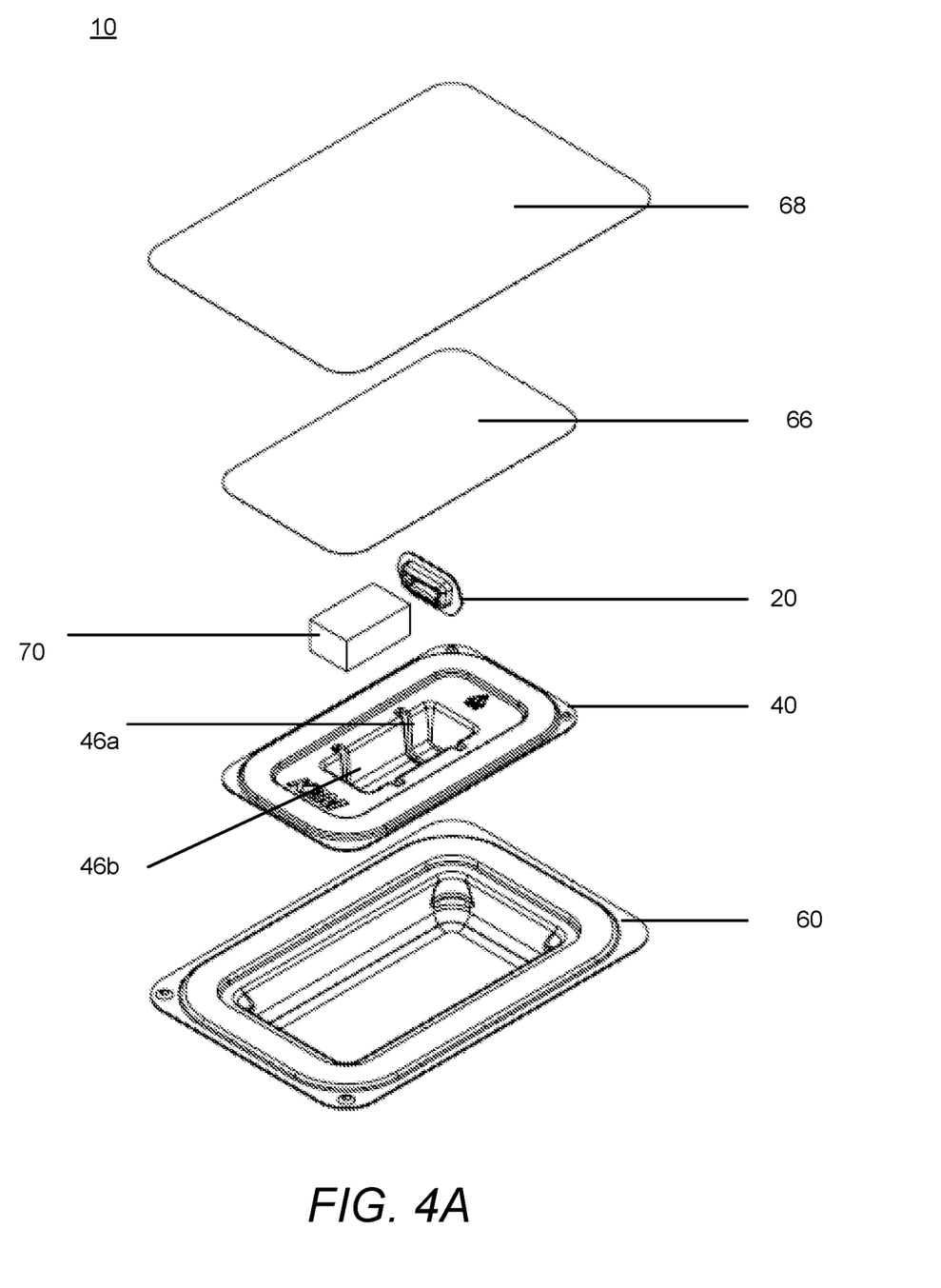
FIG. 4A is an exploded view of a package with at least one bumper according to an aspect of the invention.
Figure 4B:
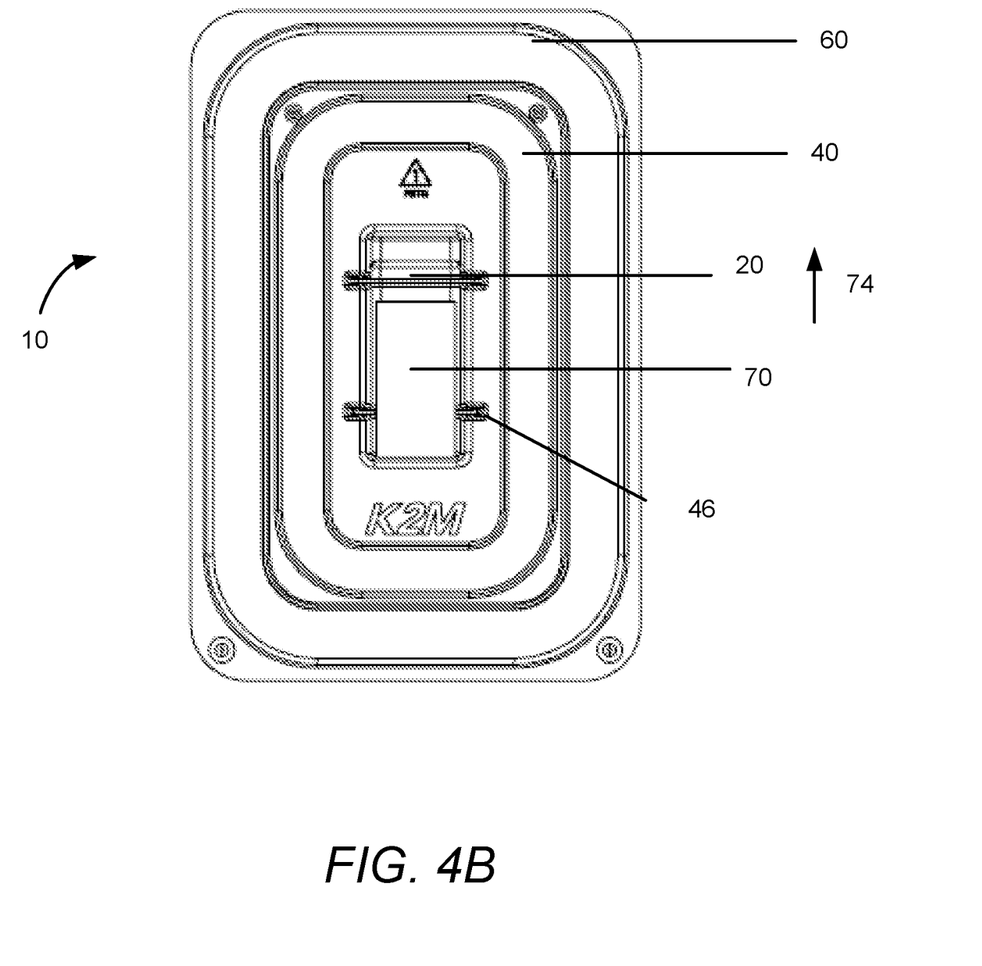
FIG. 4B is a top view of FIG. 4A.

The package 10 can include at least one bumper 20. In an aspect, the package 10 can include any number of bumpers 20, such as at least two bumpers, at least three bumpers, etc. In an aspect, the number of bumpers 20 can correspond to the number of grooves 46 present in the first cavity 44 of the first tray 40. The package 10 can include any number of bumpers 20 to hold a medical device 70. In an aspect, the package 10 can include one bumper 20 to hold a medical device 70, as shown in FIGS. 4A-4B. In another aspect, the package 10 can include two bumpers 20a, 20b to securely hold a medical device 70 that is smaller in size, as shown in FIGS. 5A-7B. In another aspect, the package 10 can include zero bumpers 2 because the size of the medical device 70 minimally fits within the first cavity 44 of the first tray 40.

As shown in FIGS. 2A-2D, the package 10 can include a first tray 40 having a first cavity 44 that extends from a second front 42 along the second plane 32 (e.g., x-axis). In an aspect, the first cavity 44 can be configured and dimensioned to be any depth that can fit within a size defined by the second cavity 62 of the second tray 60. In an aspect, the first cavity 44 can be configured and dimensioned to be any length and/or width that can fit within a size defined by the second cavity 62 of the second tray 60. In another aspect, the first cavity 44 can be configured and dimensioned to be any size that fits a medical device 70. The first cavity 44 of the first tray 40 can nest within the second cavity 62 of the second tray 60.

Figure 2A:
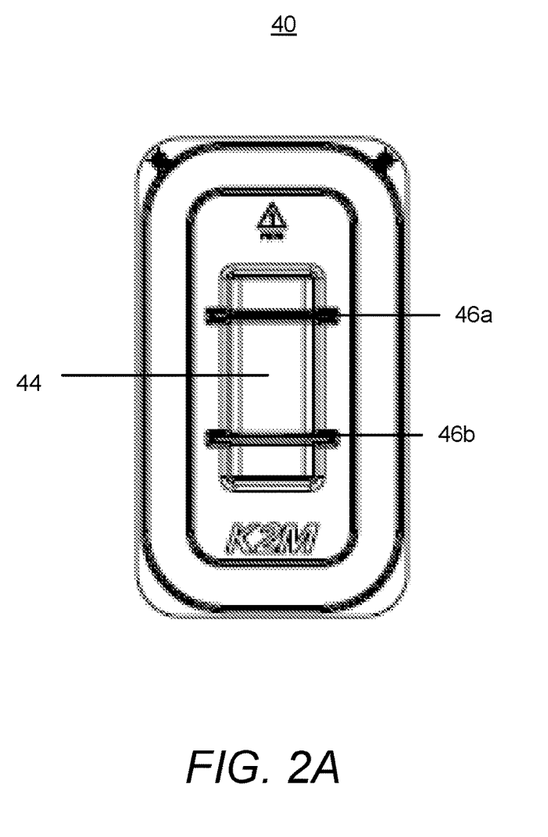
FIG. 2A is a top view of a first tray according to an aspect of the invention.
Figure 2B:
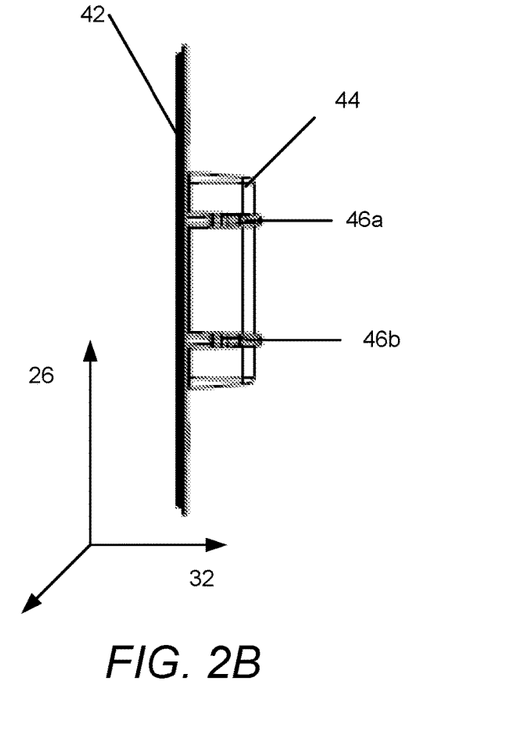
FIG. 2B is a side view of FIG. 2A.
Figure 2C:
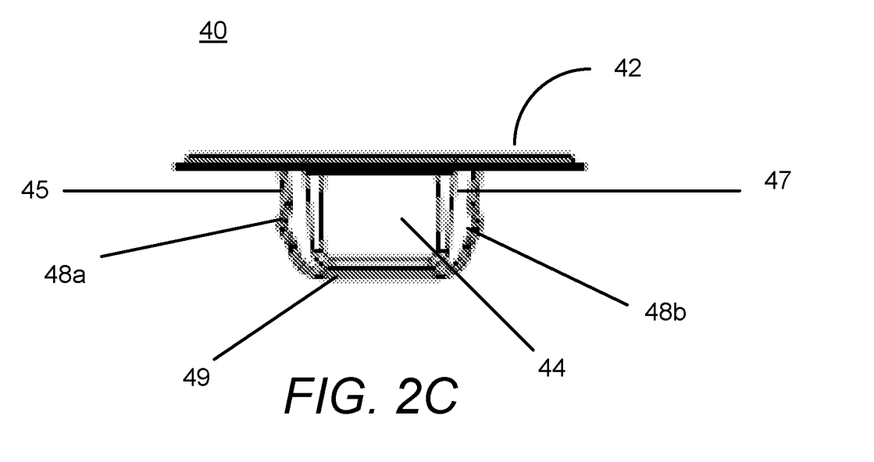
FIG. 2C is a front view of FIG. 2A.
Figure 2D:
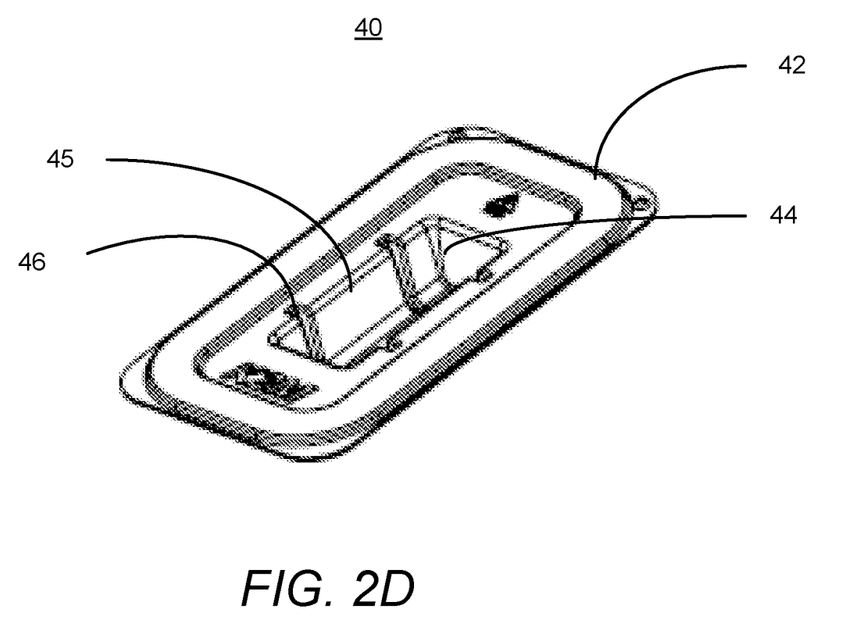
FIG. 2D is an isometric view of FIG. 2A.

As shown in FIGS. 2A, 2B, and 2D, the first cavity 44 can include at least one groove 46a, 46b configured and dimensioned to receive the at least one bumper 20. In an aspect, the at least one groove 46 can protrude from at least one of a first side 45, a second side 47, and a third side 49 of the first cavity 44, as shown in FIG. 2C. In another aspect, the at least one groove 46 can protrude from the first cavity 44 on at least two sides 45, 47, and can include at least one notch 48, as shown in FIG. 2C. The first side 45 can include a notch 48a. The second side 47 can include a notch 48b. The third side 49 can protrude from the first cavity 44 in an amount sufficient to engage the first front 30 of the bumper 20.

In another aspect, the at least one groove 46 can be configured and dimensioned to receive at least one bumper 20 having a reverse taper (not shown). The at least one groove 46 can include a reverse notch that would correspond to a reverse taper of the at least one bumper 20. The at least one groove 46 having a reverse notch can be configured and dimensioned to engage with the corresponding reverse taper of the at least one bumper 20.

The first cavity 44 can include any number of grooves 46. In an aspect, the number of grooves 46 can correspond to the number of bumpers 20 included with the package 10. The first cavity 44 can include any number of grooves 46 to securely hold any number of bumpers 20. In an aspect, the first cavity 44 can include at least one groove 46a. In another aspect, the first cavity 44 can include at least two grooves 46a, 46b. In a further aspect, the first cavity 44 can include at least three grooves 46a, 46b, 46c, etc.

The first cavity 44 can be configured and dimensioned to receive a medical device 70, as shown in FIGS. 4A-7B. The first cavity 44 can be any length, width, and depth to receive a medical device 70. The first cavity 44 can be configured and dimensioned to receive at least one bumper 20 in various configurations. The at least one bumper 20 can be inserted in a first direction 72 into at least one groove 46a of the first cavity 44, as shown in FIGS. 4A-B. The at least one bumper 20 can be inserted in a second direction 74 into a least one groove 46a of the first cavity.

Figure 5A:
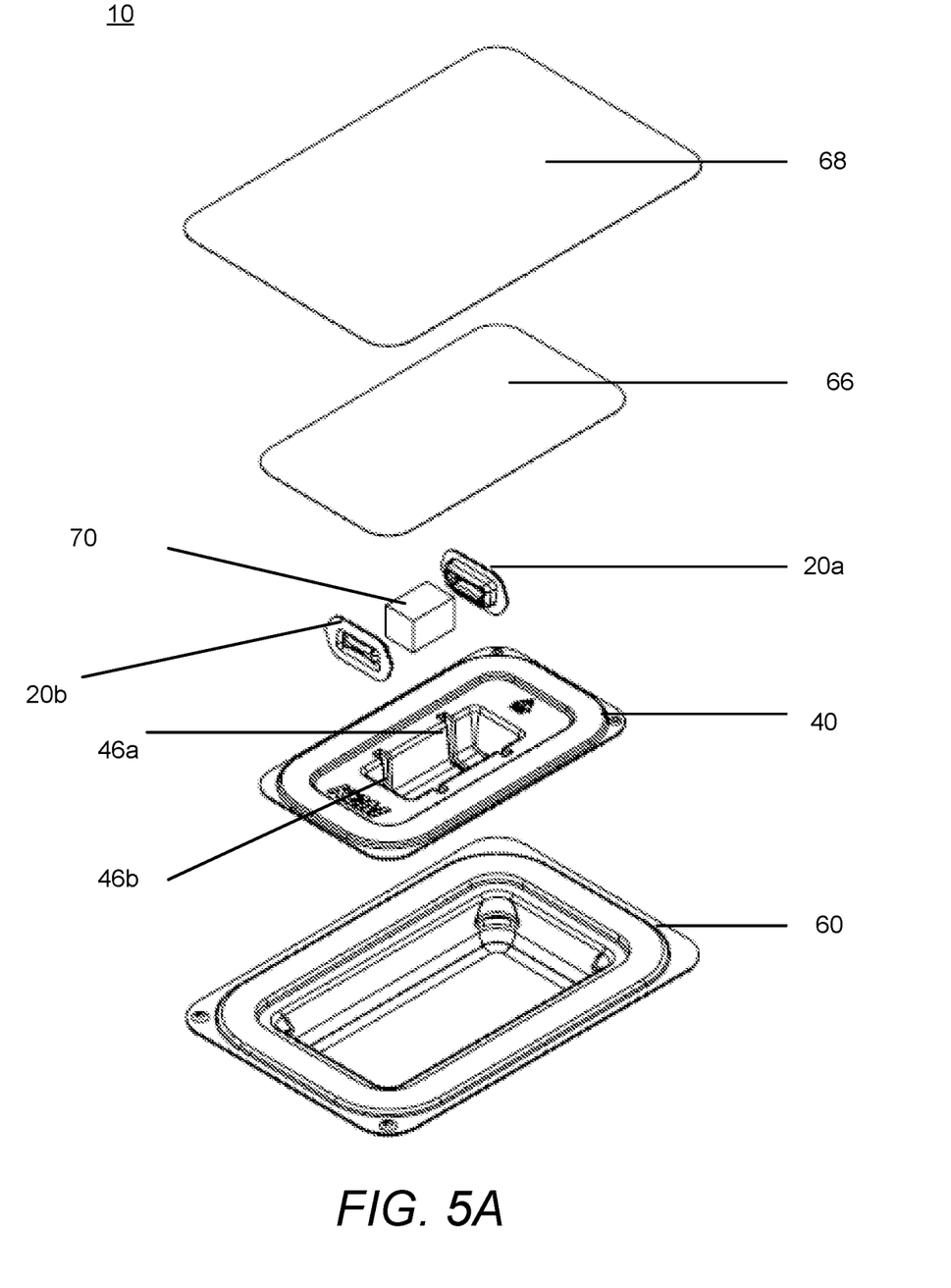
FIG. 5A is an exploded view of a package with at least one bumper according to an aspect of the invention.
Figure 5B:
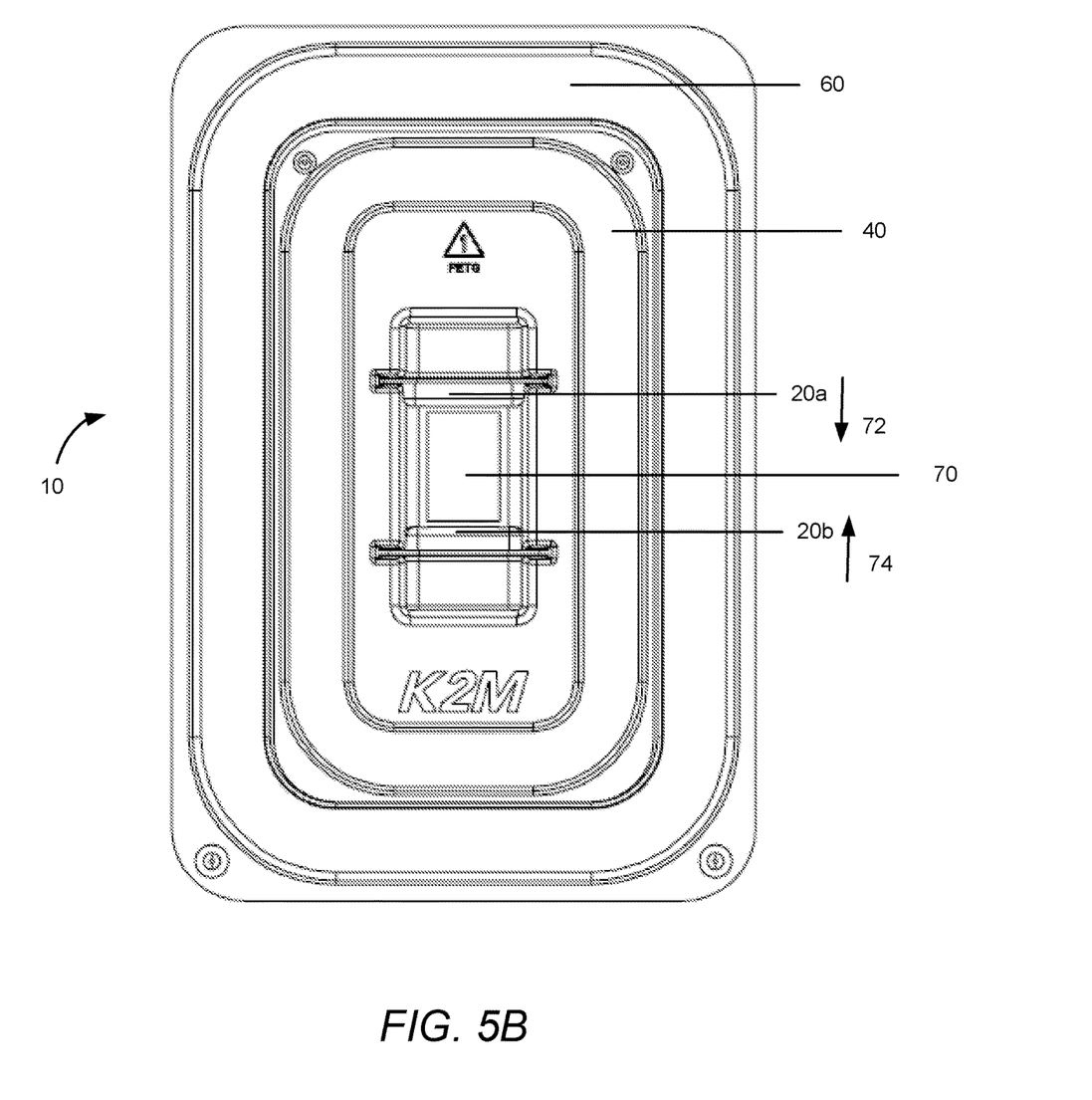
FIG. 5B is a top view of FIG. 5A.
Figure 6A:
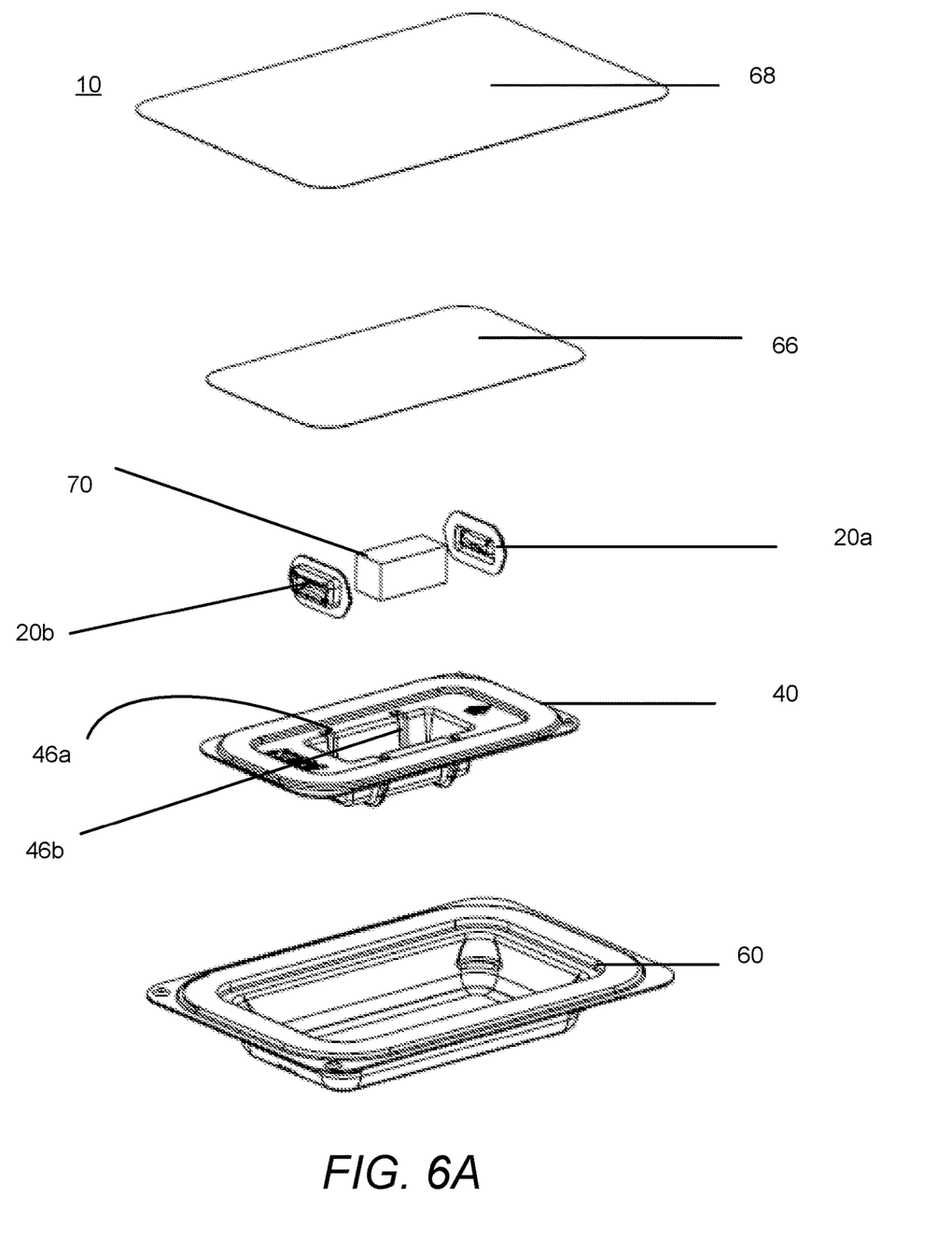
FIG. 6A is an exploded view of a package with at least one bumper according to an aspect of the invention.
Figure 6B:
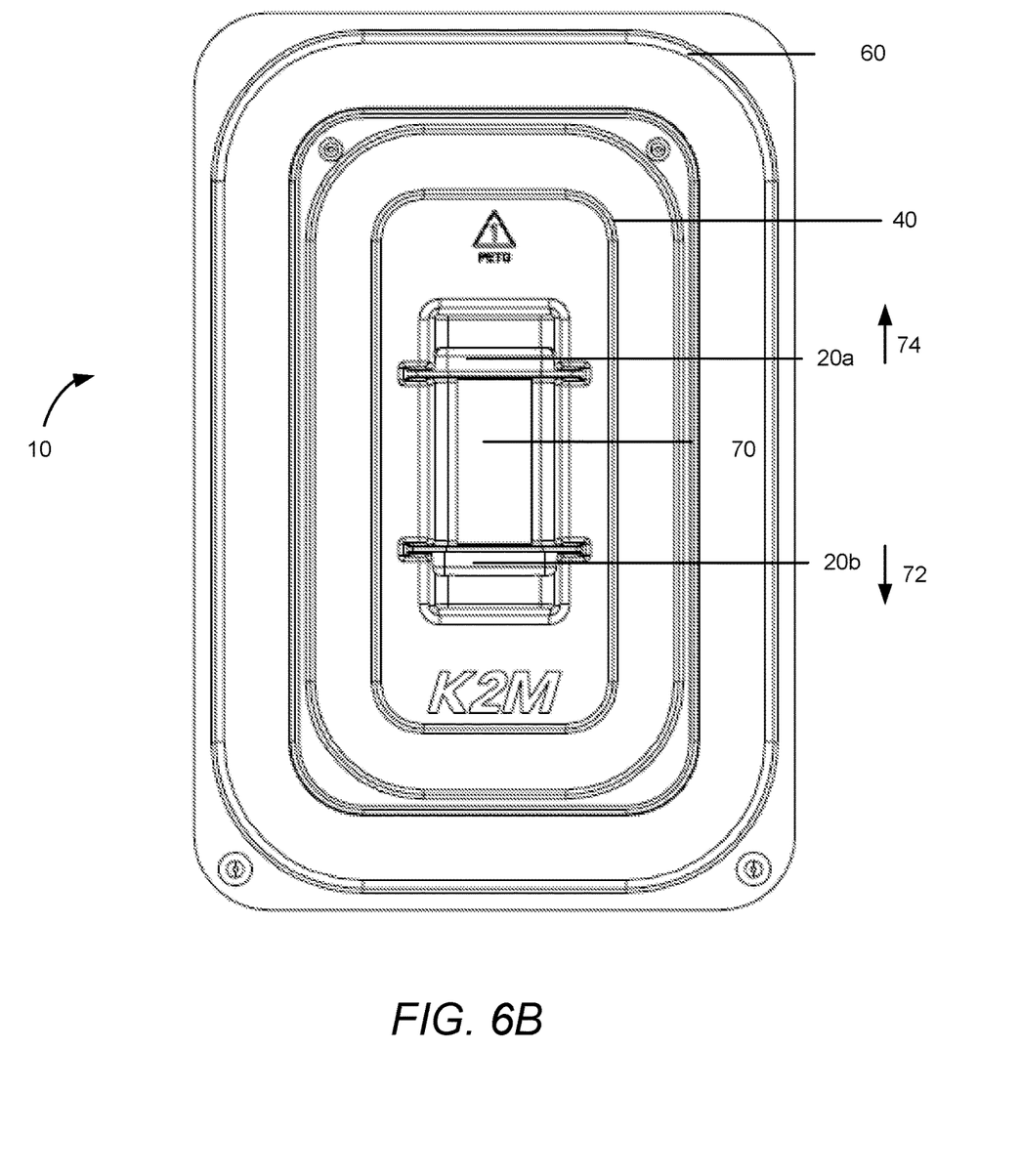
FIG. 6B is a top view of FIG. 6A.
Figure 7A:
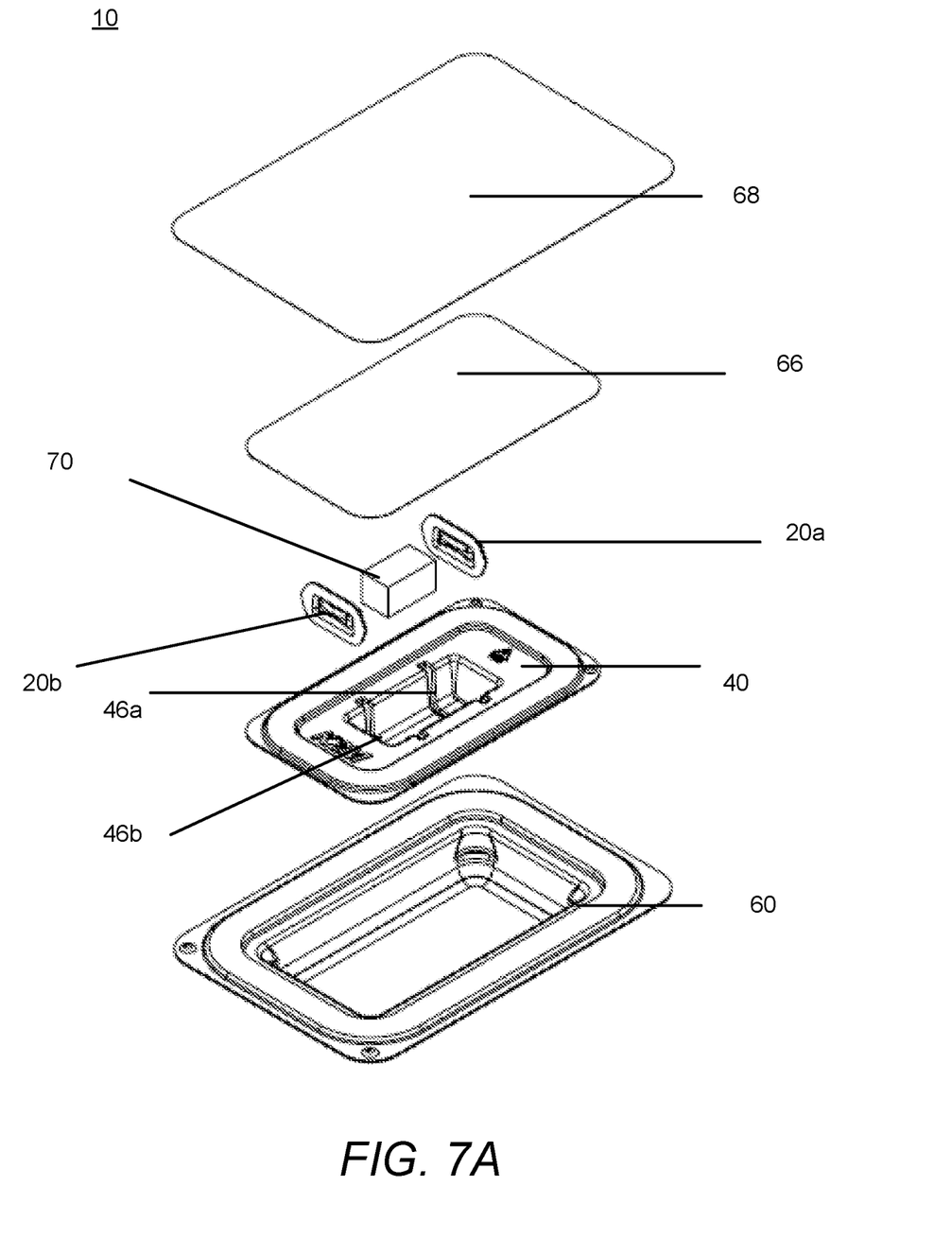
FIG. 7A is an exploded view of a package with at least one bumper according to an aspect of the invention.
Figure 7B:
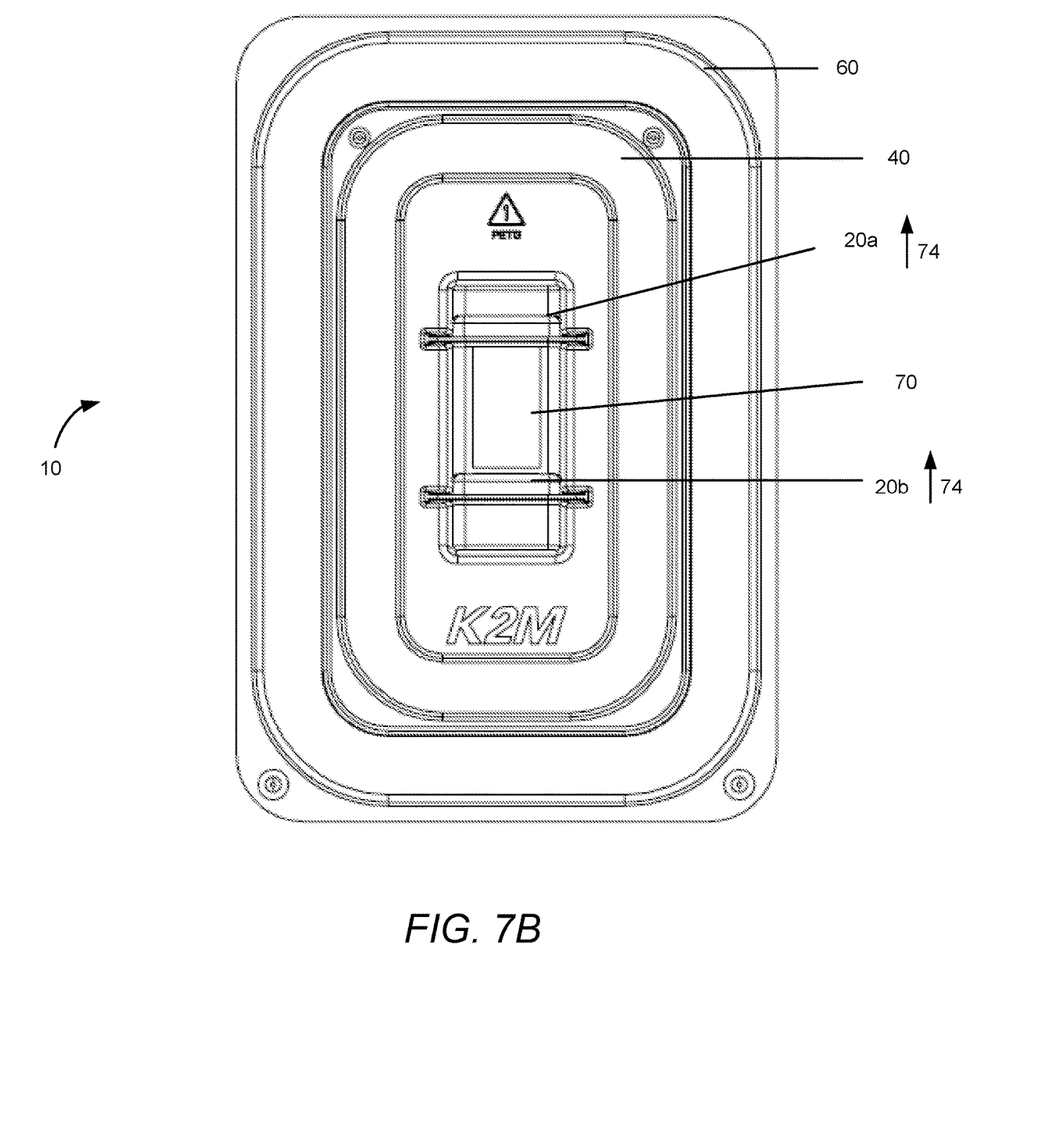
FIG. 7B is a top view of FIG. 7A.

As shown in FIGS. 7A-7B, in an aspect, the first cavity 44 can include two grooves 46a, 46b, wherein one bumper 20a can be inserted in a second direction 74 into one of the two grooves, and wherein one bumper 20b can be inserted in the second direction 74 into the other of the two grooves. Similarly, the bumpers 20a, 20b can be inserted in a first direction 72 in both of the two grooves 46a, 46b. As shown in FIGS. 6A-6B, in another aspect, the first cavity 44 can include two grooves 46a, 46b, wherein one bumper 20b can be inserted in a first direction 72 into one of the two grooves, and wherein one bumper 20a can be inserted in a second direction 74 into the other of the two grooves. As shown in FIGS. 5A-5B, in an aspect, the first cavity 44 can include two grooves 46a, 46b, wherein one bumper 20a can be inserted in a first direction 72 into one of the two grooves, and wherein one bumper 20b can be inserted in the second direction 74 into the other of the two grooves.

Figure 3A:
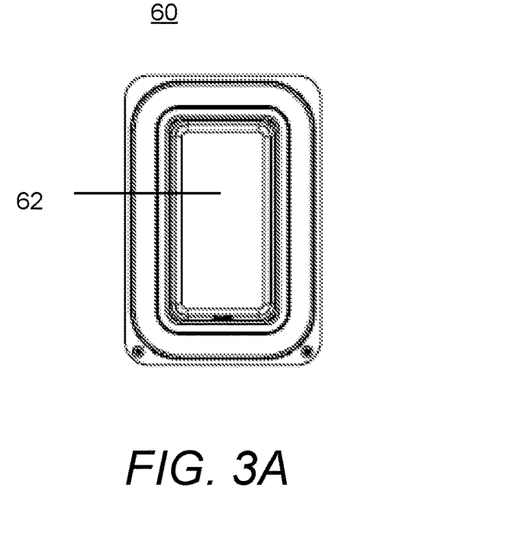
FIG. 3A is a top view of a second tray according to an aspect of the invention.
Figure 3B:
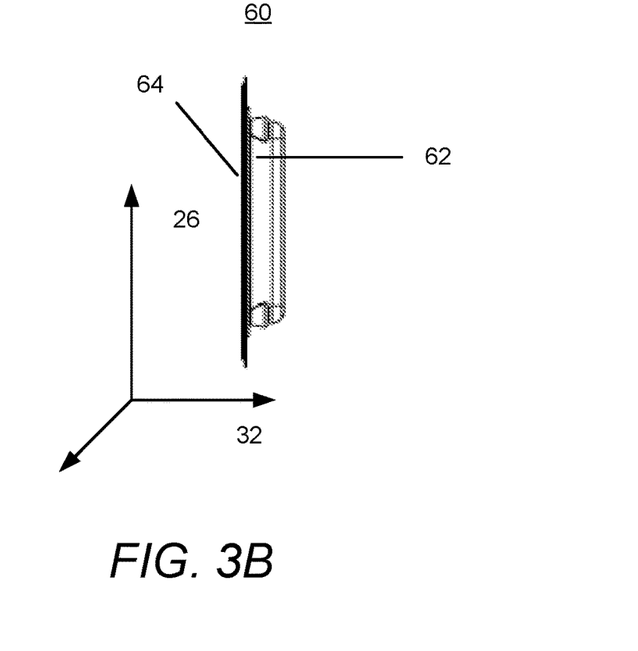
FIG. 3B is a side view of FIG. 3A.
Figure 3C:
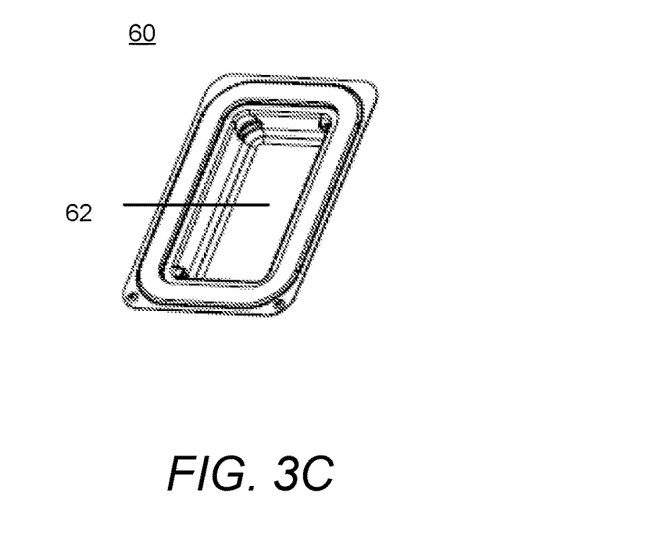
FIG. 3C is a perspective view of FIG. 3A.

The package 10 can also include a second tray 60. The second tray 60 can include a second cavity 62 that extends from a third front 64 along the second plane 32 (e.g., the x-axis), as shown in FIGS. 3A-3C. The second cavity 62 can be configured and dimensioned to receive the first cavity 44 of the first tray 40.

The package 10 can also include at least one additional part, such as a first lid 66, and a second lid 68, as shown in FIGS. 4A, 5A, 6A, and 7A. The first lid 66 can engage with the second front 42 of the first tray 40. In an aspect, the first lid 66 and the first tray 40 can form a first sealed container. The second lid 68 can engage with the third front 64 of the second tray 60. In an aspect, the second lid 68 and the second tray 60 can form a second sealed container.

A medical device 70 can be inserted into the first cavity 44 of the first tray 40. At least one bumper 20 can be inserted into the at least one groove 46 of the first tray 44. The at least one bumper 20 can be inserted in either a first direction 72 or a second direction 74 into the at least one groove 46 of the first cavity 44 of the first tray 40 depending upon the size of the medical device 70. A second bumper 20 can also be inserted in either a first direction 72 or a second direction 74 depending upon the size of the medical device 70. In an aspect, the at least one bumper 20 should be inserted in a manner to securely hold the medical device 70 within the first cavity 44. A first lid 66 can be applied to the first tray 40 to form a first sealed container containing a medical device 70, for example creating a single barrier sterile package. The first cavity 44 of the first tray 40 can then be inserted into the second cavity 62 of the second tray 60. A second lid 68 can be applied to the second tray 60 to form a second sealed container containing the sealed first tray, for example creating a double barrier sterile package. The package 10 can be a double sterile package, wherein the sealed first tray 40 contains a medical device 70, and the sealed second tray 60 contains the sealed first tray 40.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

The invention claimed is:

1. A package comprising:
 a tray including a peripheral edge and a cavity, the cavity having a plurality of side surfaces separating the peripheral edge from a bottom surface of the cavity, the cavity including a first groove in a first side surface of the plurality of side surfaces of the cavity and a second groove in a bottom surface of the cavity; and
 a bumper having a perimeter defined by an external edge, only a portion of the external edge being operatively disposed within at least one of the first groove and the second groove.

2. The package of claim 1, wherein the bumper includes a length extending from a first end to a second end along a first plane and a protrusion along a second plane transverse to the first plane.

3. The package of claim 2, wherein the portion of the external edge of the bumper does not include the protrusion.

4. The package of claim 2, wherein the bumper is operatively disposed in the at least one groove in one of a first orientation relative to the tray and a second orientation relative to the tray, the first orientation being 180 degrees relative to the second orientation.

5. The package of claim 2, wherein the protrusion is entirely within the cavity when the portion of the external edge is operatively disposed in the at least one groove.

6. The package of claim 1, wherein the tray includes a peripheral surface surrounding the cavity, the peripheral surface abutting the peripheral edge, and wherein the bumper is received in the first groove and the second groove.

7. The package of claim 6, wherein the at least one groove includes two grooves in opposing side surfaces of the plurality of side surfaces and the bumper is operatively disposed in each of the two grooves.

8. The package of claim 6, wherein the at least one groove extends continuously in three surfaces of the cavity including a first side surface of the plurality of side surfaces, the bottom surface, and a second side surface opposite the first side surface, the bumper operatively disposed in the at least one groove in each of the three surfaces.

9. The package of claim 1, wherein the at least one groove includes a first groove and a second groove, the first groove parallel to and offset from the second groove, and wherein the bumper includes a first bumper and a second bumper, the first bumper operatively disposed in the first groove and the second bumper operatively disposed in the second groove.

10. The package of claim 9, wherein the first bumper includes a first protrusion and the second bumper includes a second protrusion, the first protrusion facing toward a first end of the tray and the second protrusion facing away from the first end of the tray.

11. The package of claim 1, wherein the bumper alters an interior dimension of the cavity.

12. The package of claim 1, wherein the cavity is fully enclosed within a perimeter of the tray.

13. A package comprising:
 a tray having a cavity, the cavity including at least one groove in a surface of the cavity; and
 a bumper having an inner portion and an outer portion surrounding the inner portion, the inner portion including a protrusion having sides shaped to provide increased strength relative to a remainder of the bumper,
 wherein a thickness of the inner portion is different from a thickness of the outer portion, and
 wherein the outer portion defines a perimeter of the bumper and less than an entirety of the outer portion of the bumper is operatively disposed within the at least one groove.

14. The package of claim 13, wherein the outer portion of the bumper is planar.

15. The package of claim 13, wherein the tray includes a peripheral surface surrounding the cavity and the cavity includes a plurality of side surfaces separating the peripheral surface from a bottom surface of the cavity, the at least one groove in at least one of the plurality of side surfaces.

16. The package of claim 15, wherein the at least one groove extends continuously in three surfaces of the cavity including a first side surface of the plurality of side surfaces, the bottom surface, and a second side surface opposite the first side surface, the bumper operatively disposed in the at least one groove in each of the three surfaces.

17. The package of claim 13, wherein the inner portion protrudes from one side of the outer portion, the inner portion entirely within the cavity of the tray and facing an edge of the cavity closest to the at least one groove when disposed in the at least one groove, the edge of the cavity being parallel to the bumper.

18. The package of claim 13, wherein the at least one groove includes a first groove and a second groove, the first groove parallel to and offset from the second groove, and wherein the bumper includes a first bumper and a second bumper, the first bumper operatively disposed in the first groove and the second bumper operatively disposed in the second groove.

19. The package of claim 18, wherein the first bumper includes a first protrusion and the second bumper includes a second protrusion, the first protrusion facing toward a first end of the tray and the second protrusion facing away from the first end of the tray.

20. The package of claim 18, wherein the first bumper includes a first protrusion and the second bumper includes a second protrusion, the first protrusion facing toward a first end of the tray and the second protrusion facing toward the first end of the tray.

* * * * *